US008857988B2

(12) United States Patent
Sharma et al.

(10) Patent No.: US 8,857,988 B2
(45) Date of Patent: Oct. 14, 2014

(54) DATA ACQUISITION METHODS FOR REDUCED MOTION ARTIFACTS AND APPLICATIONS IN OCT ANGIOGRAPHY

(75) Inventors: Utkarsh Sharma, San Ramon, CA (US); Matthew J. Everett, Livermore, CA (US)

(73) Assignee: Carl Zeiss Meditec, Inc., Dublin, CA (US)

( * ) Notice: Subject to any disclaimer, the term of this patent is extended or adjusted under 35 U.S.C. 154(b) by 6 days.

(21) Appl. No.: 13/542,588

(22) Filed: Jul. 5, 2012

(65) Prior Publication Data

US 2013/0176532 A1  Jul. 11, 2013

Related U.S. Application Data

(60) Provisional application No. 61/505,483, filed on Jul. 7, 2011, provisional application No. 61/645,464, filed on May 10, 2012.

(51) Int. Cl.
*A61B 3/10* (2006.01)
*A61B 5/00* (2006.01)

(52) U.S. Cl.
CPC .............. *A61B 3/102* (2013.01); *A61B 5/0066* (2013.01)
USPC ............................ 351/209; 351/206; 351/246

(58) Field of Classification Search
USPC ............... 351/200–246; 396/18, 51; 600/425; 382/130, 131
See application file for complete search history.

(56) References Cited

U.S. PATENT DOCUMENTS

| 4,135,791 A | 1/1979 | Govignon |
| 4,213,678 A | 7/1980 | Pomerantzeff et al. |
| 4,732,466 A | 3/1988 | Humphrey |
| 4,768,873 A | 9/1988 | Webb |
| 4,768,874 A | 9/1988 | Webb et al. |
| 4,856,891 A | 8/1989 | Pflibsen et al. |
| 4,937,526 A | 6/1990 | Ehman et al. |
| 5,321,501 A | 6/1994 | Swanson et al. |
| 5,471,303 A | 11/1995 | Ai et al. |
| 5,575,286 A | 11/1996 | Weng et al. |
| 5,644,642 A | 7/1997 | Kirschbaum |

(Continued)

FOREIGN PATENT DOCUMENTS

| EP | 2147634 A1 | 1/2010 |
| WO | 03/105678 A2 | 12/2003 |

(Continued)

OTHER PUBLICATIONS

International Search Report and Written Opinion received for PCT Patent Application No. PCT/EP2012/063191, mailed on Dec. 4, 2012, 8 pages.

(Continued)

*Primary Examiner* — Darryl J Collins
*Assistant Examiner* — Gary O'Neill
(74) *Attorney, Agent, or Firm* — Morrison & Foerster LLP

(57) ABSTRACT

Systems and methods for reducing the effects of motion on functional optical coherence tomography (OCT) imaging are described. Embodiments including post-processing and motion tracking are presented. A preferred embodiment in which functional OCT data is collected and analyzed for motion as a multiple scan unit is described. An extension of the invention to the collection of large field of view or montaged functional OCT data sets is also presented.

19 Claims, 4 Drawing Sheets

(56) References Cited

U.S. PATENT DOCUMENTS

| | | | |
|---|---|---|---|
| 5,729,008 | A | 3/1998 | Blalock et al. |
| 5,767,941 | A | 6/1998 | Ferguson |
| 5,920,373 | A | 7/1999 | Bille |
| 5,943,115 | A | 8/1999 | Ferguson |
| 5,975,697 | A | 11/1999 | Podoleanu et al. |
| 6,283,954 | B1 | 9/2001 | Yee |
| 6,295,374 | B1 | 9/2001 | Robinson et al. |
| 6,325,512 | B1 | 12/2001 | Wei |
| 6,501,551 | B1 | 12/2002 | Tearney et al. |
| 6,552,796 | B2 | 4/2003 | Magnin et al. |
| 6,556,853 | B1 | 4/2003 | Cabib et al. |
| 6,655,805 | B2 | 12/2003 | Fujieda |
| 6,726,325 | B2 | 4/2004 | Xie et al. |
| 6,736,508 | B2 | 5/2004 | Xie et al. |
| 6,758,564 | B2 | 7/2004 | Ferguson |
| 6,769,769 | B2 | 8/2004 | Podoleanu et al. |
| 6,788,421 | B2 | 9/2004 | Fercher et al. |
| 6,927,860 | B2 | 8/2005 | Podoleanu et al. |
| 7,072,047 | B2 | 7/2006 | Westphal et al. |
| 7,113,818 | B2 | 9/2006 | Podoleanu et al. |
| 7,118,216 | B2 | 10/2006 | Roorda |
| 7,133,137 | B2 | 11/2006 | Shimmick |
| 7,145,661 | B2 | 12/2006 | Hitzenberger |
| 7,301,644 | B2 | 11/2007 | Knighton et al. |
| 7,330,270 | B2 | 2/2008 | O'Hara et al. |
| 7,365,856 | B2 | 4/2008 | Everett et al. |
| 7,404,640 | B2 | 7/2008 | Ferguson et al. |
| 7,458,684 | B2 | 12/2008 | Fukuma et al. |
| 7,480,396 | B2 | 1/2009 | Teiwes et al. |
| 7,512,436 | B2 | 3/2009 | Petty et al. |
| 7,527,378 | B2 | 5/2009 | Fukama et al. |
| 7,643,154 | B2 | 1/2010 | Kikawa et al. |
| 7,755,769 | B2 | 7/2010 | Everett et al. |
| 7,756,311 | B2 | 7/2010 | Yasuno et al. |
| 7,777,893 | B2 | 8/2010 | Kikawa et al. |
| 7,789,511 | B2 | 9/2010 | Aoki et al. |
| 7,805,009 | B2 | 9/2010 | Everett et al. |
| 8,018,598 | B2 | 9/2011 | Cense et al. |
| 8,050,504 | B2 | 11/2011 | Everett et al. |
| 8,115,935 | B2 | 2/2012 | Everett et al. |
| 8,363,958 | B2 | 1/2013 | Everett et al. |
| 8,649,611 | B2 | 2/2014 | Everett et al. |
| 2002/0085208 | A1 | 7/2002 | Hauger et al. |
| 2003/0103212 | A1 | 6/2003 | Westphal et al. |
| 2003/0199769 | A1 | 10/2003 | Podoleanu et al. |
| 2003/0227631 | A1 | 12/2003 | Rollins et al. |
| 2005/0024586 | A1 | 2/2005 | Teiwes et al. |
| 2005/0140984 | A1 | 6/2005 | Hitzenberger |
| 2005/0219544 | A1 | 10/2005 | Chan et al. |
| 2005/0270486 | A1 | 12/2005 | Teiwes et al. |
| 2006/0171503 | A1 | 8/2006 | O'Hara et al. |
| 2006/0228011 | A1 | 10/2006 | Everett et al. |
| 2007/0291277 | A1 | 12/2007 | Everett et al. |
| 2008/0025570 | A1* | 1/2008 | Fingler et al. ............... 382/107 |
| 2008/0100612 | A1 | 5/2008 | Dastmalchi et al. |
| 2009/0141240 | A1 | 6/2009 | Weitz et al. |
| 2009/0168017 | A1 | 7/2009 | O'Hara et al. |
| 2010/0053553 | A1 | 3/2010 | Zinser |
| 2010/0118132 | A1 | 5/2010 | Yumikake et al. |
| 2011/0267581 | A1 | 11/2011 | Nakajima et al. |
| 2011/0299034 | A1 | 12/2011 | Walsh et al. |
| 2012/0033181 | A1 | 2/2012 | Koizumi et al. |
| 2012/0120408 | A1 | 5/2012 | Yasuno et al. |
| 2012/0140175 | A1 | 6/2012 | Everett et al. |
| 2012/0274783 | A1* | 11/2012 | Ko et al. ............... 348/169 |

FOREIGN PATENT DOCUMENTS

| | | | |
|---|---|---|---|
| WO | 2004/055473 | A1 | 1/2004 |
| WO | 2008/002839 | A2 | 1/2008 |
| WO | 2010/119913 | A1 | 10/2010 |
| WO | 2012/130976 | A1 | 10/2012 |

OTHER PUBLICATIONS

U.S. Appl. No. 13/433,127, filed Mar. 28, 2012, Narasimha-Iyer et al., titled "Systems and Methods for Efficiently Obtaining Measurements of the Human Eye Using Tracking", 42 pages.

U.S. Appl. No. 13/458,933, filed Apr. 27, 2012, Horn et al., titled "Ultra Wide-Field Optical Coherence Tomography", 21 pages.

Klein et al., "The Effect of (Micro-) Saccades on the Image Quality of Ultrawide-Field Multimegahertz OCT Data", SPIE Photonices West, 8209-13, Session 4, 2012, p. 82.

Leitgeb et al., "Ultrahigh Resolution Fourier Domain Optical Coherence Tomography", Optics Express, vol. 12, No. 10, pp. 2156-2165.

Li et al., "Automatic Montage of SD-OCT Data Sets", Optics Express, vol. 19, No. 27, Dec. 19, 2011, pp. 26239-26248.

Zawadzki et al., "Cellular Resolution Volumetric in vivo Retinal Imaging with Adaptive Optics—Optical Coherence Tomography", Optics Express, vol. 17, No. 5, Mar. 2, 2009, pp. 4084-4094.

Office Action received for European Patent Application No. 06723850.1, mailed on Dec. 23, 2009, 3 pages.

International Search Report and Written Opinion received for PCT Patent Application No. PCT/EP2006/002883, mailed on Nov. 28, 2006, 12 pages.

International Search Report and Written Opinion received for PCT Patent Application No. PCT/EP2012/055684, mailed on Jul. 5, 2012, 13 pages.

Non Final Office Action received for U.S. Appl. No. 11/389,351, mailed on Dec. 10, 2009, 12 pages.

Notice of Allowance received for U.S. Appl. No. 11/389,351, mailed on Jun. 7, 2010, 4 pages.

Notice of Allowance received for U.S. Appl. No. 12/075,477, mailed on Mar. 8, 2010, 7 pages.

Non Final Office Action received for U.S. Appl. No. 12/794,926, mailed on Apr. 4, 2011, 10 pages.

Notice of Allowance received for U.S. Appl. No. 12/794,926, mailed on Oct. 11, 2011, 9 pages.

Non-Final Office Action received for U.S. Appl. No. 12/861,672, mailed on Feb. 23, 2011, 9 pages.

Notice of Allowance received for U.S. Appl. No. 12/861,672, mailed on Jul. 13, 2011, 5 pages.

Notice of Allowance received for U.S. Appl. No. 13/276,203, mailed on Sep. 26, 2012, 8 pages.

Non-Final Office Action received for U.S. Appl. No. 13/739,193, mailed on Jun. 13, 2013, 6 pages.

Boer et al., "Improved Signal-To-Noise Ratio in Spectral-Domain Compared with Time-Domain Optical Coherence Tomography", Optics Letters, vol. 28, No. 21, Nov. 1, 2003, pp. 2067-2069.

Choma et al., "Sensitivity Advantage of Swept Source and Fourier Domain Optical Coherence Tomography", Optics Express, vol. 11, No. 18, Sep. 8, 2003, pp. 2183-2189.

Ehman et al., "Adaptive Technique for High-Definition MR Imaging of Moving Structures", Radiology, vol. 173, No. 1, Oct. 1989, pp. 255-263.

Hammer et al., "Advanced Scanning Methods with Tracking Optical Coherence Tomography", Optics Express, vol. 13, No. 20, Oct. 3, 2005, pp. 7937-7947.

Hammer et al., "Active Retinal Tracker for Clinical Optical Coherence Tomography Systems", Journal for Biomedical Optics, vol. 10, No. 2, Mar./Apr. 2005, pp. 024038-1-024038-11.

Hammer et al., "Image Stabilization for Scanning Laser Ophthalmoscopy", Optics Express, vol. 10, No. 26, Dec. 30, 2002, pp. 1542-1549.

Hitzenberger et al., "Three-Dimensional Imaging of the Human Retina by High-Speed Optical Coherence Tomography", Optics Express, vol. 11, No. 21, Oct. 20, 2003, pp. 2753-2761.

Huang et al., "Optical Coherence Tomography", Science, vol. 254, Nov. 22, 1991, pp. 1178-1181.

Ip et al., "Fundus Based Eye Tracker for Optical Coherence Tomography", Proceedings of the 26th Annual International Conference of the IEEE EMBS, Sep. 1-5, 2004, pp. 1505-1508.

Joergensen et al., "Reducing Speckle Noise in Retinal Oct Images by Aligning Multiple B-Scans", Coherence Domain Optical Methods and Optical Coherence Tomography in Biomedicine VIII, Proceedings of the SPIE, vol. 5316, 2004, pp. 205-213.

(56) References Cited

OTHER PUBLICATIONS

Leitgeb et al., "Performance of Fourier Domain vs. Time Domain Optical Coherence Tomography", Optics Express, vol. 11, No. 8, Apr. 21, 2003, pp. 889-894.

Mulligan, Jeffrey B., "Recovery of Motion Parameters from Distortions in Scanned Images", Proceedings of the NASA Image Registration Workshop (IRW97), 1997, 15 pages.

Naess et al., "Computer-Assisted Laser Photocoagulation of the Retina-A Hybrid Tracking Approach", Journal of Biomedical Optics, vol. 7, No. 2, Apr. 2002, pp. 179-189.

Nassif et al., "In Vivo High-Resolution Video-Rate Spectral-Domain Optical Coherence Tomography of the Human Retina and Optic Nerve", Optics Express, vol. 12, No. 3, Feb. 9, 2004, pp. 367-376.

Podoleanu et al., "Combined Multiplanar Optical Coherence Tomography and Confocal Scanning Ophthalmoscopy", Journal of Biomedical Optics, vol. 9, No. 1, Jan./Feb. 2004, pp. 86-93.

Podoleanu et al., "Combined Optical Coherence Tomograph and Scanning Laser Ophthalmoscope", Electronics Letters, vol. 34, No. 11, May 28, 1998, 2 pages.

Rogers et al., "Topography and Volume Measurements of the Optic Nerve Using En-Face Optical Coherence Tomography", Optics Express, vol. 9, No. 10, Nov. 5, 2001, pp. 533-545.

Stevenson et al., "Correcting for Miniature Eye Movements in High Resolution Scanning Laser Ophthalmoscopy", Ophthalmic Technologies XV, Proceedings of the SPIE, vol. 5688, 2005, pp. 145-151.

Everett et al., "Method and Apparatus for Measuring Motion of a Subject Using a Series of Partial Images from an Imaging System", Unpublished U.S. Appl. No. 13/739,193, filed Jan. 11, 2013.

Non-Final Office Action received for U.S. Appl. No. 13/357,097, mailed on Sep. 12, 2013, 9 pages.

International Preliminary Report on Patentability received for PCT Patent Application No. PCT/EP2012/055684, mailed on Oct. 10, 2013, 10 pages.

Notice of Allowance received for U.S. Appl. No. 13/357,097, mailed on Dec. 17, 2013, 10 pages.

Non Final Office Action received for U.S. Appl. No. 13/433,127, mailed on Apr. 10, 2014, 17 pages.

Notice of Allowance received for U.S. Appl. No. 13/739,193, mailed on Oct. 1, 2013, 7 pages.

Unpublished U.S. Appl. No. 14/153,993, filed Jan. 13, 2014, titled "Method and Apparatus for Measuring Motion of a Subject Using a Series of Partial Images from an Imaging System". (copy not attached).

Unpublished U.S. Appl. No. 14/242,683, filed Apr. 1, 2014, titled "Method of Motion Correction in Optical Coherence Tomography Imaging". (copy not attached).

International Preliminary Report on Patentability received for PCT Patent Application No. PCT/EP2012/063191, mailed on Jan. 16, 2014, 8 pages.

* cited by examiner

DATA ACQUISITION METHODS FOR REDUCED MOTION ARTIFACTS AND APPLICATIONS IN OCT ANGIOGRAPHY

PRIORITY

This application claims priority to U.S. Provisional Application Ser. No. 61/505,483 filed Jul. 7, 2011, and U.S. Provisional Application Ser. No. 61/645,464 filed May 10, 2012, both of which are hereby incorporated by reference.

TECHNICAL FIELD

One or more embodiments of the present invention relate to the field of Optical Coherence Tomography (OCT). In particular, the invention described herein provides systems and methods for achieving higher quality and larger field of view functional OCT images.

BACKGROUND

Optical coherence tomography (OCT) is a noninvasive, noncontact imaging modality that uses coherence gating to obtain high-resolution cross-sectional images of tissue microstructure. Several implementations of OCT have been developed. In Frequency domain OCT (FD-OCT), the interferometric signal between light from a reference and the back-scattered light from a sample point is recorded in the frequency domain either by using a dispersive spectrometer in the detection arm in the case of spectral-domain OCT (SD-OCT) or rapidly tuning a swept laser source in the case of swept-source OCT (SS-OCT). After a wavelength calibration, a one-dimensional Fourier transform is taken to obtain an A-line spatial distribution of the object scattering potential.

Functional OCT can provide important clinical information that is not available in the typical intensity based structural OCT images. There have been several functional contrast enhancement methods including Doppler OCT, Phase-sensitive OCT measurements, Polarization Sensitive OCT, Spectroscopic OCT, etc. Integration of functional extensions can greatly enhance the capabilities of OCT for a range of applications in medicine.

One of the most promising functional extensions of OCT has been the field of OCT angiography which is based on flow contrast. Visualization of the detailed vasculature using OCT could enable doctors to obtain new and useful clinical information for diagnosis and management of eye diseases in a non-invasive manner. Fluorescein angiography and indocyanine green (ICG) angiography are currently the gold standards for vasculature visualization in the eye. However, the invasiveness of these approaches combined with possible complications (allergy to dyes, side effects) make them unsuitable techniques for widespread screening applications in ophthalmic clinics. There are several flow contrast techniques in OCT imaging that utilize the change in data between successive B-scans or frames (inter-frame change analysis) of the OCT intensity or phase-resolved OCT data. One of the major applications of such techniques has been to generate en face vasculature images of the retina. High resolution en face visualization based on inter-frame change analysis requires high density of sampling points and hence the time required to finish such scans can be up to an order of magnitude higher compared to regular cube scans used in commercial OCT systems.

While OCT angiography appears to be an exciting technology, there are several technical limitations that need to be overcome before it can gain widespread acceptance in clinical settings. Typically, the most common approach for determining motion contrast is to obtain multiple B-scans (at the same location or closely spaced) and analyze the change in OCT data due to motion. One of the major limitations of OCT angiography is the long acquisition times and associated motion artifacts that can affect analysis. Eye motion can result in loss of data, image artifacts and hence greatly reduces the usability of the acquired data. While axial motion can be detected and compensated for, it is relatively difficult and time consuming to detect all cases of transverse motion using post-processing methods alone. Since the algorithm derives signal from the change in OCT data, even small shifts in gaze or saccadic motion of the eye could result in significant artifacts. Post-processing methods to correct for transverse motion artifacts have limited success and are often very time consuming. One of the approaches to solve this problem is to use very high speed OCT systems, however, such systems can be very complex and costly (see for example T. Klein et al., "The effect of micro-saccades on the image quality of ultrawide-field multimegahertz OCT data," SPIE Photonices West 2012, Paper #8209-13 (2012)).

Another challenge for the OCT angiography technology is to obtain retinal vasculature maps at large fields of view (FOV). The large acquisition times and huge data volumes make it impractical to obtain high resolution data over large FOVs. Acquisition of multiple smaller data cubes of smaller FOV and montaging them together using post-processing is one of the approaches that can be applied to work around this problem. Rosenfeld et al. recently demonstrated a method for automated montaging of SD-OCT data sets to generate images and analysis over larger FOV (see for example Y. Li et al., "Automatic montage of SD-OCT data sets,", Optics Express, 19, 26239-26248 (2011)). However, their method relies on post-processing registration and alignment of multiple OCT cubes based on their OCT-fundus images. There are several limitations in this method. Sufficient overlap of the scanned data is required for optimized performance of the algorithms and it must be ensures that changes in gaze do not result in missing un-scanned regions on the retina. Also, if there is some motion during the scan, it cannot be corrected using this method.

In light of the limitations in the prior art, a need exists to obtain motion artifact free OCT angiography images, especially large field of view images.

SUMMARY

In this invention, we describe and demonstrate a tracking based approach to generate reduced motion-artifact functional OCT data. Multiple OCT measurements at a given sample location can be analyzed to ascertain structural or functional changes over varying time scales. Either OCT intensity or phase-resolved OCT data can be used for such data analysis methods. OCT angiography is one such example where inter-frame analysis can be used to detect blood-flow by using motion-contrast. High-resolution OCT angiography requires long acquisition times and hence the final results are highly susceptible to errors caused by subject motion. En face vasculature images obtained by OCT angiography often contain horizontal stripe artifacts due to uncompensated lateral motion. Here we propose a method, wherein two or more OCT A-scans are obtained at the same location while the eye position is being monitored using tracking methods. With the use of eye tracking information, it is ensured that at least two or more A-scans are obtained from the same tissue location, and the difference between the two A-scans is calculated and analyzed to ascertain structural or functional changes accurately without any eye motion related artifacts. Retinal tracking information can also be used to guide acquisition of multiple cube scans with fixed offsets to create a large field-of-view (FOV) composite or montaged image. The use of retinal tracking can significantly reduce the post-processing efforts in order to create a large FOV analysis by guided montaging of smaller FOV scans during data acquisition.

In one embodiment of the invention, the repeated acquisitions required to generate contrast data are considered as a single unit or block of data that we will refer to as a 'cluster scan'. In this embodiment of the invention, the acquisition of single or integer multiples of cluster scan units is synchronized with the motion tracking update rate in order to reduce the motion artifact effects on the dynamic structural or functional change analysis of OCT data. When multiple OCT measurements are used to measure rapidly changing structural or functional information, it is imperative that all the OCT measurements within the cluster scan are obtained within a short time window to enable high resolution, precise and accurate change analysis.

One exemplary example for an application of this invention is OCT angiography, where the blood flow results in changes within the order of few milliseconds. The majority of the methods for OCT angiography acquire multiple B-scans or frames (say N repeat B-scans at the same location or closely spaced) and analyze the change in complex or intensity-only OCT data between B-scans (referred to as inter-frame analysis) due to motion. The idea being to separate scattering data due to motion from scattering data due to static elements being imaged. Hence in this case, the set of N B-scans can be considered as a cluster scan and an image based retinal tracking system can be adapted to synchronize the update rate of image frames with the time taken to acquire a cluster scan data. The synchronization of the update rate for retinal tracking algorithm with the cluster scan acquisition rate will ensure that:

1. Data acquired during an event of transverse motion is not used for motion contrast or change analysis.
2. Any cluster containing complete or partial data obtained during motion is rejected and the cluster scan is repeated after motion correction and eye stabilization.

Additionally, the instrument user has the capability to adjust the motion tolerance parameter in order to enable obtaining the data in an efficient way in the shortest possible time. We have demonstrated the implementation of the above mentioned solution and significant improvement in the OCT vasculature image quality was observed.

DETAILED DESCRIPTION

Figure 1:
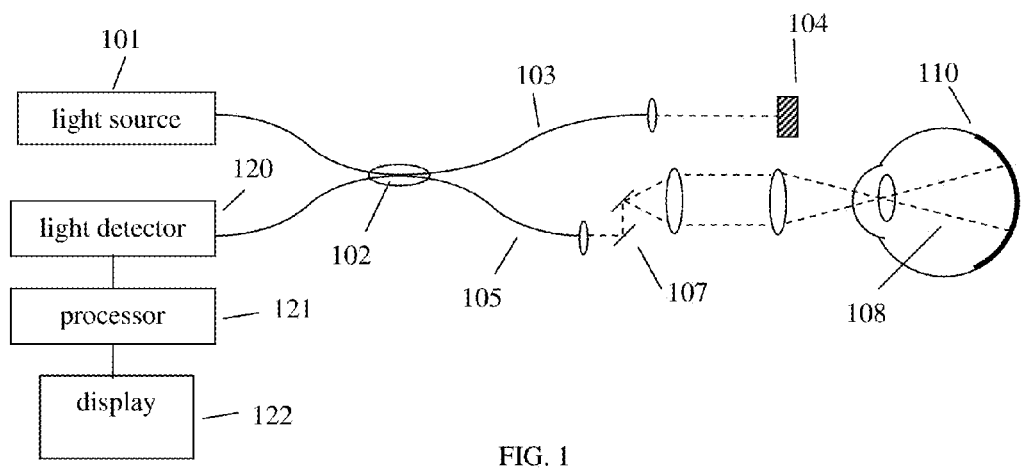
FIG. 1 is a diagram of a generalized OCT system.

A diagram of a generalized OCT system is shown in FIG. 1. Light from source 101 is routed, typically by optical fiber 105, to illuminate the sample 110, a typical sample being tissues in the human eye. The source 101 can be either a broadband light source with short temporal coherence length in the case of SD-OCT or a wavelength tunable laser source in the case of SS-OCT. The light is scanned, typically with a scanner 107 between the output of the fiber and the sample, so that the beam of light (dashed line 108) is scanned laterally (in x and y) over the area or volume to be imaged. Light scattered from the sample is collected, typically into the same fiber 105 used to route the light for sample illumination. Reference light derived from the same source 101 travels a separate path, in this case involving fiber 103 and retro-reflector 104 with an adjustable optical delay. Those skilled in the art recognize that a transmissive reference path can also be used and that the adjustable delay could be placed in the sample or reference arm of the interferometer. Collected sample light is combined with reference light, typically in a fiber coupler 102, to form light interference in a detector 120. Although a single fiber port is shown going to the detector, those skilled in the art recognize that various designs of interferometers can be used for balanced or unbalanced detection of the interference signal. The output from the detector is supplied to a processor 121. The results can be stored in the processor 121 or displayed on display 122. The processing and storing functions may be localized within the OCT instrument or functions may be performed on an external processing unit to which the collected data is transferred. This unit could be dedicated to data processing or perform other tasks which are quite general and not dedicated to the OCT device.

The sample and reference arms in the interferometer could consist of bulk-optics, fiber-optics or hybrid bulk-optic systems and could have different architectures such as Michelson, Mach-Zehnder or common-path based designs as would be known by those skilled in the art. Light beam as used herein should be interpreted as any carefully directed light path. In time-domain systems, the reference arm needs to have a tunable optical delay to generate interference. Balanced detection systems are typically used in TD-OCT and SS-OCT systems, while spectrometers are used at the detection port for SD-OCT systems. The invention described herein could be applied to anytime of OCT system capable of generating data for functional analysis.

The interference causes the intensity of the interfered light to vary across the spectrum. The Fourier transform of the interference light reveals the profile of scattering intensities at different path lengths, and therefore scattering as a function of depth (z-direction) in the sample (see for example Leitgeb et al. "Ultrahigh resolution Fourier domain optical coherence tomography," *Optics Express* 12(10):2156 (2004)). The profile of scattering as a function of depth is called an axial scan (A-scan). A set of A-scans measured at neighboring locations in the sample produces a cross-sectional image (tomogram or B-scan) of the sample. A collection of B-scans collected at different transverse locations on the sample makes up a data volume or cube. For a particular volume of data, the term fast axis refers to the scan direction along a single B-scan whereas slow axis refers to the axis along which multiple B-scans are collected. We use the term "cluster scan" herein to refer to a single unit or block of data generated by repeated acquisitions at the same location for the purposes of analyzing motion contrast. A cluster scan can consist of multiple a-scans or B-scans collected over time at a single location. A variety of ways to create B-scans are known to those skilled in the art including but not limited to along the horizontal or x-direction, along the vertical or y-direction, along the diagonal of x and y, or in a circular or spiral pattern. The majority of the examples discussed herein refer to B-scans in the x-z dimensions but the invention would apply equally to any cross sectional image.

Figure 2:
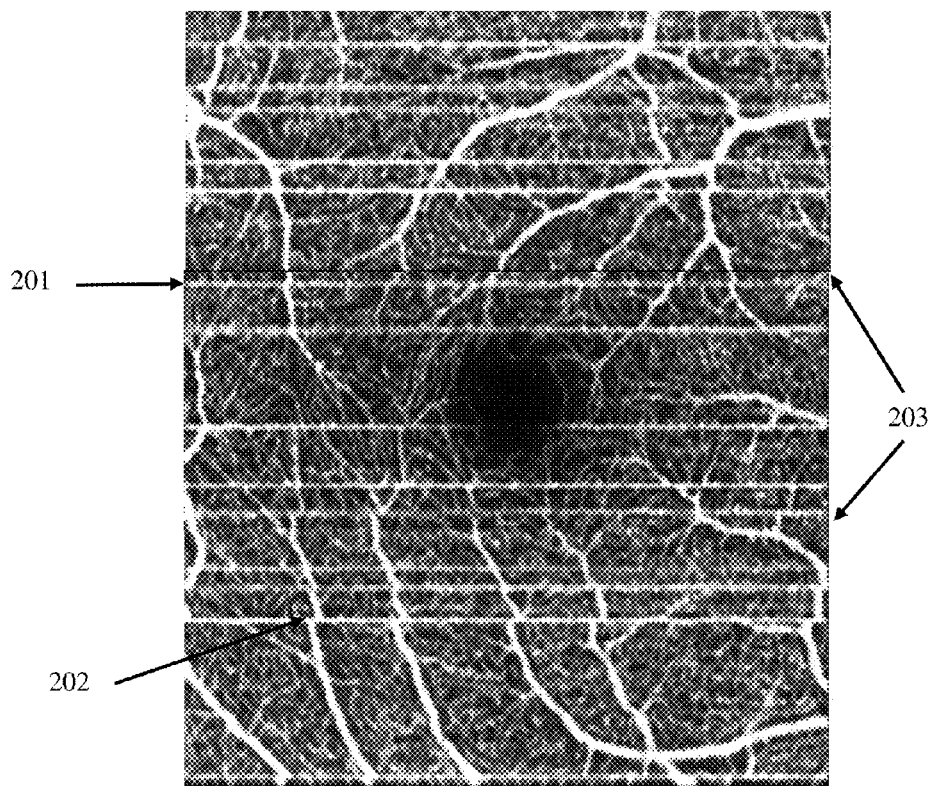
FIG. 2 shows an en face image of the retina generated from OCT data and illustrates the impact motion can have on these types of images.

In Functional OCT, differences between data collected at the same location at different times are used to analyze motion or flow. An en face vasculature image is an image displaying motion contrast signal in which the data dimension corresponding to depth is displayed as a single representative value, typically by summing or integrating an isolated portion of the data. For generating the enface images described herein, each B-scan in the given data volume consists of 300 A-scans, each cluster scan consists of four B-scans, for a total of eighty different cluster scans. Hence, the number of A-scans in a given unit data volume are 300× 80×4. After processing the data to highlight motion contrast using any one of the known motion contrast techniques, a range of 25-30 pixels corresponding to 50-60 microns of tissue depth from the surface of internal limiting membrane (ILM) in retina, are summed to generate an en face image of the vasculature. Each B-scan takes approximately 12 ms to acquire (including fly-back time) so the time between B-scans is approximately 12 ms which is on the order of interest for retinal vasculature dynamics. For the enface image shown in FIG. 2, three volumes of data were collected with some overlapping area in the retina. The enface images obtained from the three volumes were montaged or combined to create a larger field of view enface image.

For large data volume acquisitions, such as those required for motion contrast analysis, the possibility and occurrences of eye motion increases. Eye motion can result in loss of data and image artifacts, hence greatly reducing the usability of the acquired data. In the time (usually a few seconds) required to build a useful map of vasculature, the patient's gaze can shift, causing the retinal image to move from the point of view of the ophthalmic device. In the image displayed in FIG. 2, generated from data taken without any motion tracking and without any motion correction processing, there are two kinds of motion artifacts caused due to transverse eye motion that are clearly visible:

1. Horizontal line artifacts in the en face vasculature image of retina caused by small or transient transverse shifts of fixation of the eye (arrow 201)
2. Appearance of shifted blocks of data within a single cube of data caused by small changes in the fixation of the eye (arrow 202)

Figure 4:
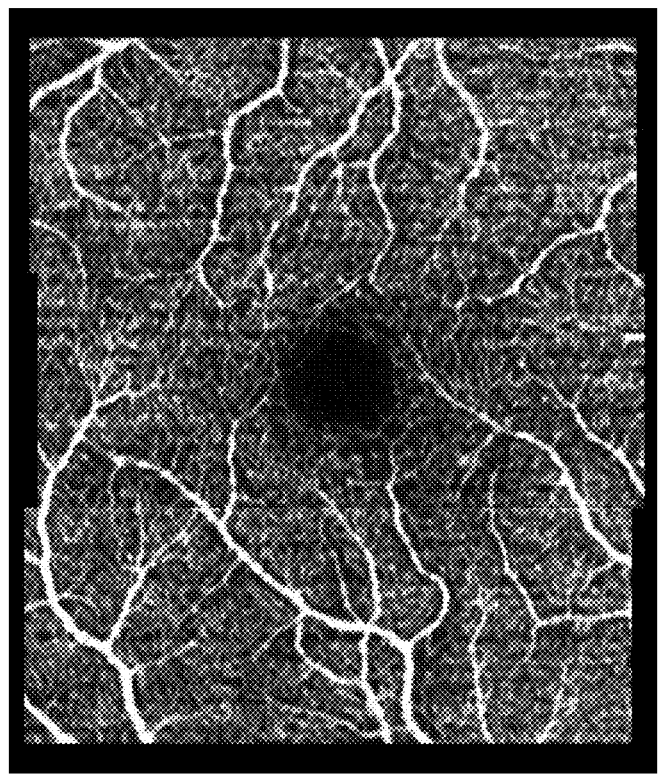
FIG. 4 shows a motion corrected en face vasculature image generated from OCT data using aspects of the present invention.

FIG. 4 was generated by collecting data according to the process outlined above. Three sets of data are collected and processed separately and montaged together in post processing to generate the en face image. The three data sets are separated by thin horizontal lines 203.

Here we describe two approaches to solve the problem caused by eye motion in OCT angiography data collection that can be incorporated into OCT systems to enable higher quality and larger field of view motion contrast images. The first is a post processing based approach in which motion correction techniques are applied to data for inter-frame analysis comprising the following steps:

a. Register the set of B-scans within a cluster scan to account for shifts in fixation.
b. Calculate the inter-frame motion-contrast information for each cluster, but only for the B-scan regions having overlap. Discard the portions of the B-scan or even entire B-scans if there is no overlap.
c. Calculate the shifts caused by changes in eye fixation and adjust the displacement of subsequent clusters or data blocks for motion corrected visualization of enface vasculature images.

Describing this approach in further detail, volumes of OCT data are collected with each volume consisting of a plurality of cluster scans taken at the same location. After data collection, a processor is used to compare the B-scans in each cluster by autocorrelation or some other registration technique known by those skilled in the art to identify matching portions. If portions are identified with differences exceeding predefined criteria, those portions can be excluded from further analysis. This could result in full B-scans or clusters being excluded. Any one of a variety of motion contrast techniques (phase contrast, Doppler variance, OMAG, etc) can then be applied to the matched B-scans to determine the motion contrast within the sample during the collection of the data. If a loss of fixation was found to extend beyond the time required to acquire a single cluster, the amount of the motion shift can be determined and used to shift subsequent clusters in a data volume.

While post processing methods may be helpful, there are however, a few limitations of this method. Firstly, this post-processing effort could be very time consuming and intensive. Secondly, while post processing based registration can correct for motion along the fast scan axis, it will not be effective if the motion happens along the slow scan direction.

The second and preferred approach involves the use of retinal tracking during scan acquisition. Retinal tracking can be very useful to remove subject motion artifacts for motion-contrast OCT imaging. Retinal tracking can be used to acquire two or more OCT A-scans from the same location while simultaneously monitoring the eye position. Hence differences between at least two of these scans can be measured accurately to determine motion contrast, as tracking ensures that the scans are acquired from the same position. The invention described herein can apply to any tracking system capable of detecting motion of the eye. As will be discussed in further detail below, there are several known mechanisms for retinal tracking during OCT data acquisition such as use of a fundus imaging modality (CSLO, SLO etc.) or use of OCT itself to correct for motion.

Figure 3:
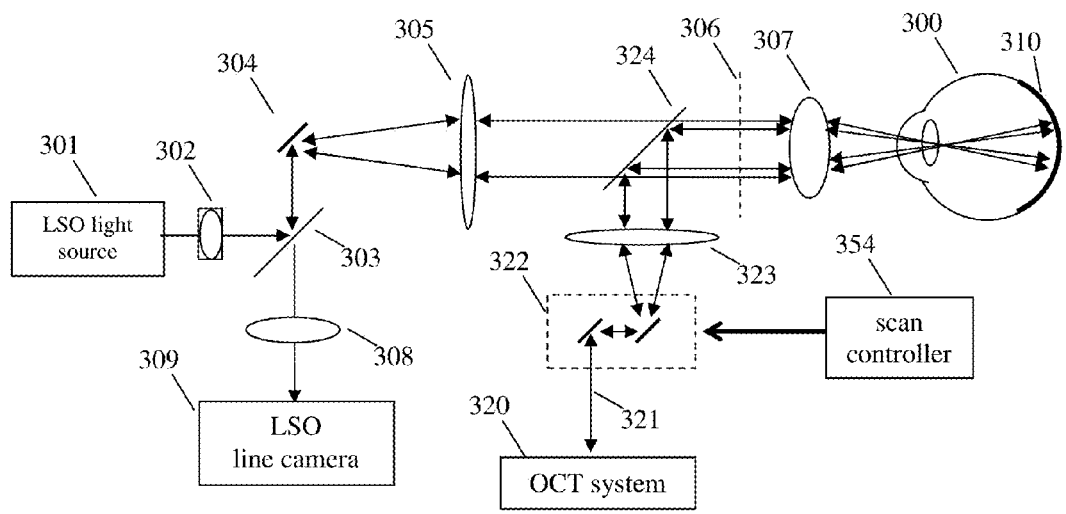
FIG. 3 shows a diagram of a combined OCT scanner and a line-scan ophthalmoscope (LSO).

A specific tracked OCT data collection system combining an OCT scanner and a line-scan ophthalmoscope (LSO) is described in U.S. Pat. No. 7,805,009 hereby incorporated by reference and illustrated in FIG. 3. In this system, light from the LSO light source 301 is routed by cylindrical lens 302 and beamsplitter 303 to scanning minor 304. The cylindrical lens 302 and the scan lens 305 produce a line of illumination at the retinal image plane 306, and the ocular lens 307 and optics of the human eye 300 re-image this line of illumination onto the retina 310. The line of illumination is swept across the retina as the scanning mirror 304 rotates. Reflected light from the retina approximately reverses the path of the LSO illumination light; the reflected light is scanned by the LSO scan mirror 304 so that the illuminated portion of the retina is continuously imaged by imaging lens 308 onto the LSO line camera 309. The LSO line camera converts the reflected LSO light into a data stream representing single-line partial images, which can be processed to form both eye tracking in formation and a real-time display of the retina.

The OCT system 320 incorporates the light source, light detector or detectors, interferometer and processor required to determine the depth profile of backscattered light from the OCT beam 321 as illustrated and described for FIG. 1. OCT scanner 322 sweeps the angle of the OCT beam laterally across the surface in two dimensions (x and y), under the control of scan controller 354. Scan lens 323 brings the OCT beam into focus on the retinal image plane 306. Beamsplitter 324 combines the OCT and LSO beam paths so that both paths can more easily be directed through the pupil of the human eye 300. (Combining the beam paths is not required in direct imaging applications, where the object itself lies in the location of the retinal image plane 306.) If the OCT and LSO use different wavelengths of light, beamsplitter 324 can be implemented as a dichroic minor. The OCT beam is re-focused onto the retina through ocular lens 307 and the optics of the human eye 300. Some light scattered from the retina follows the reverse path of the OCT beam and returns to the OCT system 320, which determines the amount of scattered light as a function of depth along the OCT beam.

In this case, the LSO image is used to provide feedback to the OCT system while collecting data for functional OCT analysis. It is critical to maintain the precise location for repeat measurements because small displacements between multiple repeat measurements obtained for change analysis can give erroneous results. While a series of A or B-scans are collected, the LSO image stream can be used to maintain a specific location on the retina so that when the data is processed with a motion contrast technique, differences are calculated between scans taken at the same location so that the highest quality image can be obtained. Tracking further enables precise positioning of multiple cluster scans so that cubes or volumes of data can be collected with precise location information minimizing the post-processing time and effort to generate final images as will be described in further detail below. In this embodiment the LSO image update rate could be arbitrary as long as the tracking mechanism ensures that at least two measurements performed for the change analysis are obtained from the same spatial location.

In a further embodiment of the invention using retinal tracking, the simultaneous LSO based retinal tracking can be adapted to synchronize the update rate of LSO frames with the time taken to acquire a single cluster scan. This will ensure that the temporal spacing between the multiple measurements within the cluster scan is uniform, resulting in more accurate calculation of changes in signal.

To illustrate the concept, here we define several parameters for each imaging modality for their respective scans:

1. Fundus Imaging Generation Period ($T_{FI}$): The time period required to generate one fundus image.
2. Fundus Imaging Duty Cycle ($F_{DC}$): The fundus imaging modality may not operate at 100% duty cycle and hence the effective fundus imaging update time is given by: $T_{FI}/F_{DC}$.
3. OCT Cluster Data Acquisition Time ($T_{CLUSTER}$): The time period required for the OCT imaging system to finish acquisition of a single cluster scan comprising of a given number of repeated B-scans at the same or closely spaced locations. This time also includes the flyback times, and settling times for the scanners.
4. Synchronization Condition: The effective fundus imaging update time ($T_{FI}/F_{DC}$) should be equal to an integral multiple of the OCT Cluster Data Acquisition Time ($T_{CLUSTER}$):

$$T_{FI} = F_{DC} \cdot T_{CLUSTER}$$

The fundus imaging duty cycle can be adjusted to the above condition. Another alternative could be to have multiple fundus imaging updates during the acquisition of a single cluster, but ensuring that the entire cluster is discarded and scanned again if the motion happened during the acquisition of the cluster. A more generalized synchronization condition would be:

$$T_{FI} = \left(\frac{M}{N}\right) \cdot F_{DC} \cdot T_{CLUSTER},$$

where M and N are integer numbers.

Once the synchronization condition is satisfied, the retinal tracking based acquisition would result in motion artifact free data acquisition for OCT angiography by providing the ability to analyze and reject data on a cluster by cluster basis. An image generated using this technique is shown in FIG. 4. A composite scan pattern consisting of three data cubes in the vertical direction (3×1) was used to generate the enface vasculature image in FIG. 4. Each cube has 80 sets of 4 cluster scans with each B-scan in the cluster scans having 300 A-scans (300×80×4). Motion artifacts such as horizontal line artifacts and shifted blocks of OCT data shown in FIG. 2 have been corrected by use of retinal tracking. The enface image from each cube was montaged automatically using an auto-correlation based approach. The tracking system utilized had an accuracy of approximately 50 microns. The middle data cube was shifted laterally by approximately 50 microns to achieve the best match.

While the embodiment above describes a tracking mechanism in which a second imaging modality is used to monitor the eye position for possible motion, the scope of this invention is not limited to any specific tracking method and an OCT measurement could provide the basis of the tracking. A central idea of this invention is the use of tracking methods to obtain repeat measurements at the same location in order to generate high quality functional contrast in OCT images.

Figure 5:
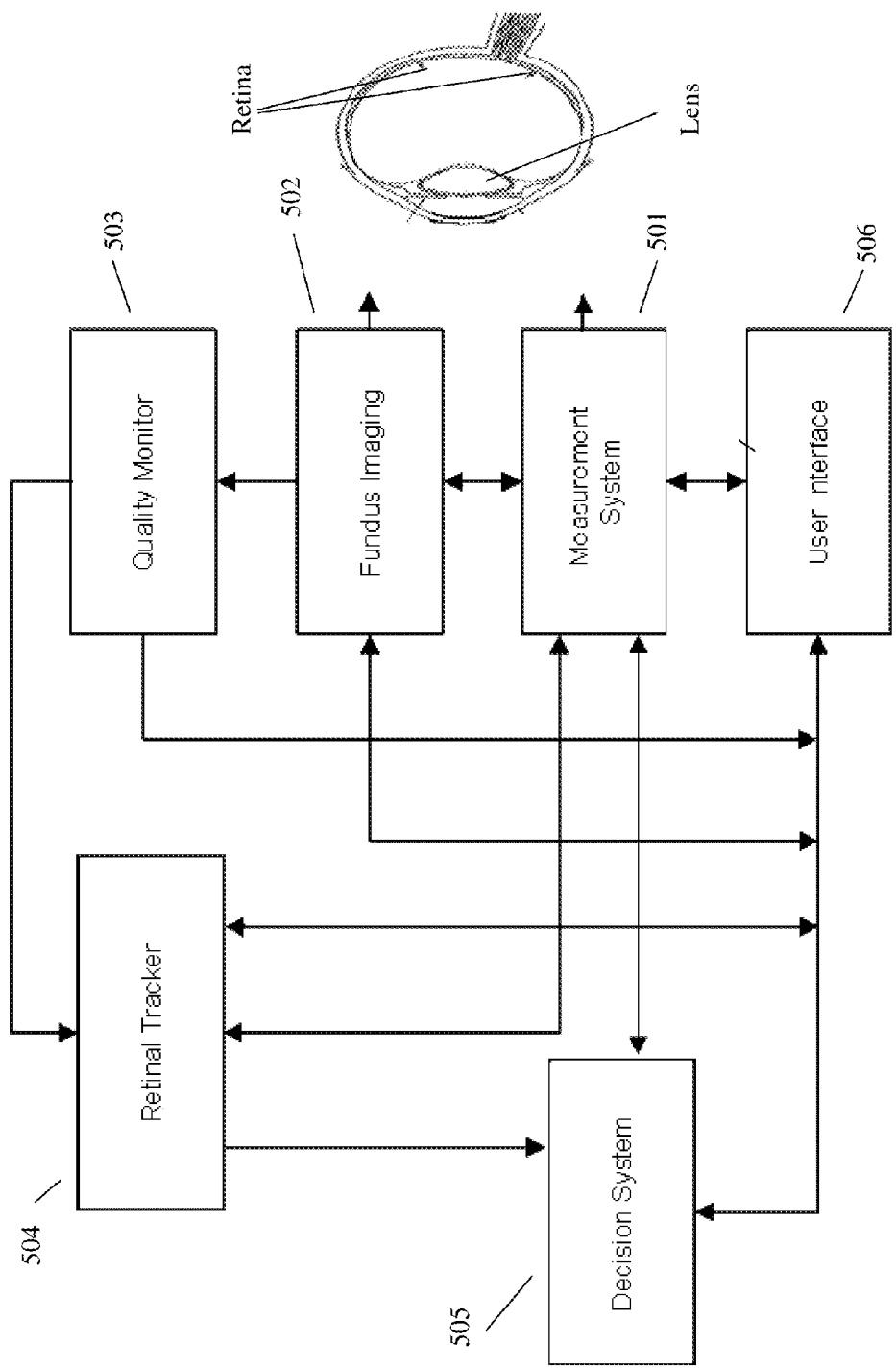
FIG. 5 shows a block diagram of a preferred tracking system for use with the present invention.

Several variants of retina tracking have been proposed and are used to follow and correct for eye motion, and hence can be applied to this invention. For example, systems have been described that detect apparent motion of the retina using a tracking beam and move minors in the imaging path to provide a stabilized OCT image (see for example U.S. Pat. Nos. 6,736,508, 6,726,325 and 6,325,512). U.S. Pat. No. 7,805, 009 as discussed above describes the use of a line scan ophthalmoscope to monitor the position of the eye and apply a correction to the OCT scanner. Even with tracking or registration, there are however, situations that cause some of the measurement data to be unusable. The methods described above do not address the problem of missing data caused by events such as blinking of eye and rapid shifts of gaze in a saccadic motion. The method described in U.S. patent application Ser. No. 13/433,127 filed Mar. 28, 2012 hereby incorporated by reference, overcomes one or more of the above-identified limitations. The system includes the following elements as illustrated in FIG. 5:

1. A measurement system 501 for acquiring ophthalmic measurements.
2. An imaging system 502 (LSO, cSLO, etc.) that produces images of the retina to be used by the tracking system to analyze motion.
3. A synchronization mechanism between (1) and (2).
4. A quality monitoring system 503 that analyzes the images of the eye to decide if they are of sufficient quality for tracking purposes, additionally this system helps to select the best image to be used as a reference image for the tracking system described next.
5. A retinal tracking system 504 capable of determining if the retina has moved based on a comparison to a reference image or frame. The retinal tracking system can detect motion in any or all of the x,y, and z dimensions.
6. A decision system 505 that decides based on the input from the retinal tracking system 504, the measurement system 501, and some other pre-defined criteria whether the acquired data is acceptable. If it is acceptable, the measurement data is stored in memory. If it is not, it instructs the measurement system to go back and rescan the data optionally with computed offsets to compensate for motion.

7. A user interface system 506 that displays relevant information to the user and gets inputs from the user for the different systems as needed.

A key aspect of this tracking method is the decision system 505. It provides the ability to determine when to go back and re-scan the measurement data based on different inputs to the system or when to continue on with data collection if the scan has exceeded a predetermined amount of time. This is important for motion contrast imaging as it is desirable to collect the multiple scans in a cluster scan in a restricted amount of time with ideally even spacings between the multiple scans.

In our preferred embodiment of the present invention for generation of flow-contrast images, N repeated measurements are taken at the same location with the tracking method described above that is capable of re-scanning or continuing data collection based on the decision system. The system could be designed with preset criteria or allow the user to input criteria that will collect high quality functional OCT data. In using this system, it is ensured that:

1. Data acquired during an event of bulk transverse motion is not used for motion contrast analysis.
2. Any cluster containing complete or partial data obtained during motion is rejected and the location is re-scanned after motion correction.
3. The user has the capability to adjust the motion tolerance parameter in order to enable the collection of data in an efficient way in the shortest possible time.

Retinal Tracking Based Composite Scan Patterns to Obtain Large Field of View Images In another embodiment of this invention, we propose using retinal tracking for generating multiple scans with fixed offsets to create a large field-of-view (FOV) composite or montaged image using several en face images of vasculature in retina. Li et al. recently demonstrated a method for automated montaging of SD-OCT data sets to generate images and analysis over larger FOV (see for example Y. Li et al., "Automatic montage of SD-OCT data sets,", Optics Express, 19, 26239-26248 (2011)). However, their method relies on post-processing registration and alignment of multiple OCT cubes based on their OCT-fundus images. The multiple OCT cubes were acquired with small overlaps and the montaging was done for the full 3-D volume. However, there are several limitations in this method. Sufficient overlap of the scanned data is required for optimized performance of the algorithms and to ensure that changes in gaze does not result in missing un-scanned regions on the retina. Also, if there is some motion during the scan, it cannot be corrected by this method.

Figure 6:
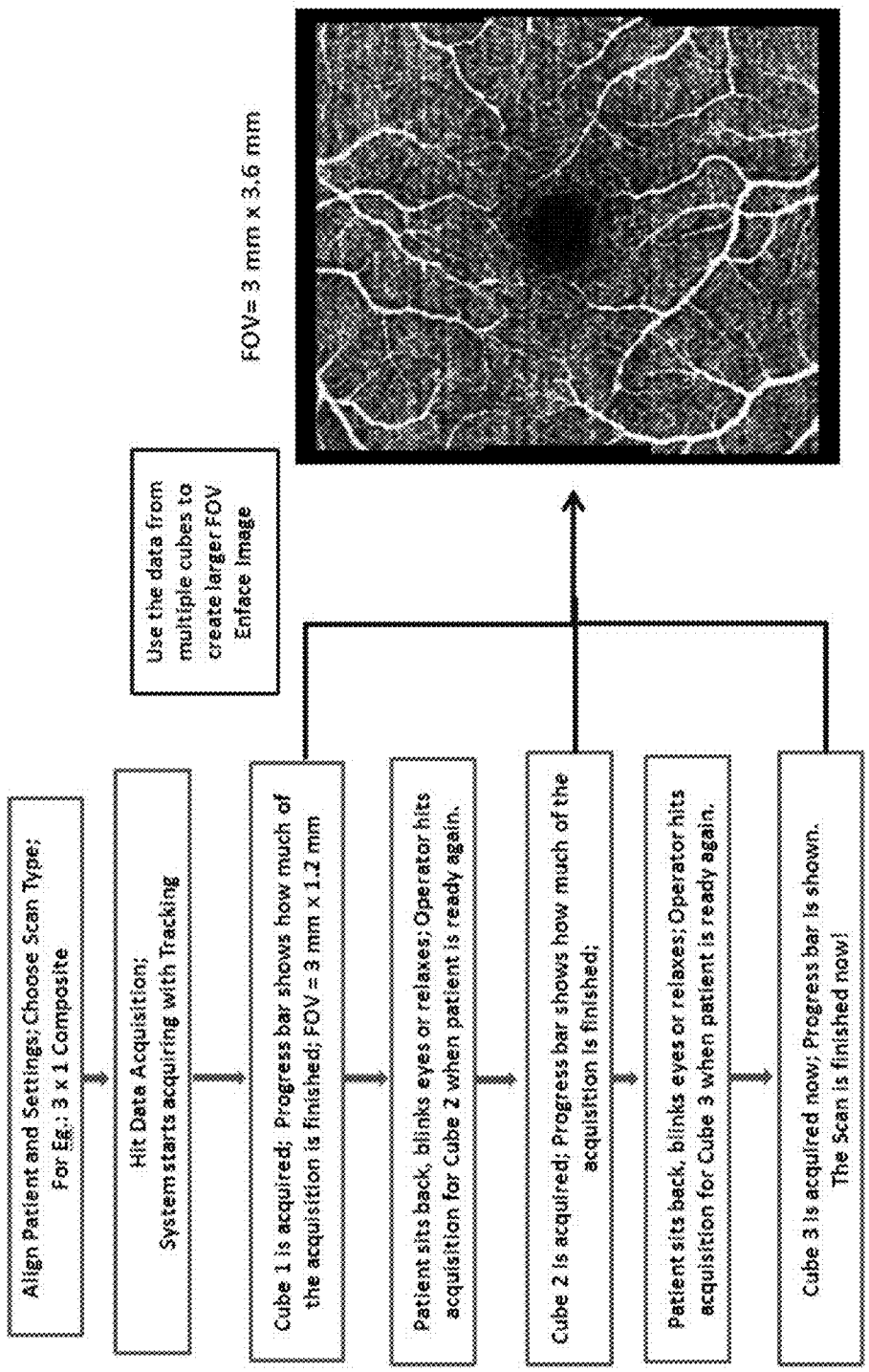
FIG. 6 illustrates a series of steps that could be used to generate a montaged en face vasculature image according to the present invention.
Figure 5:
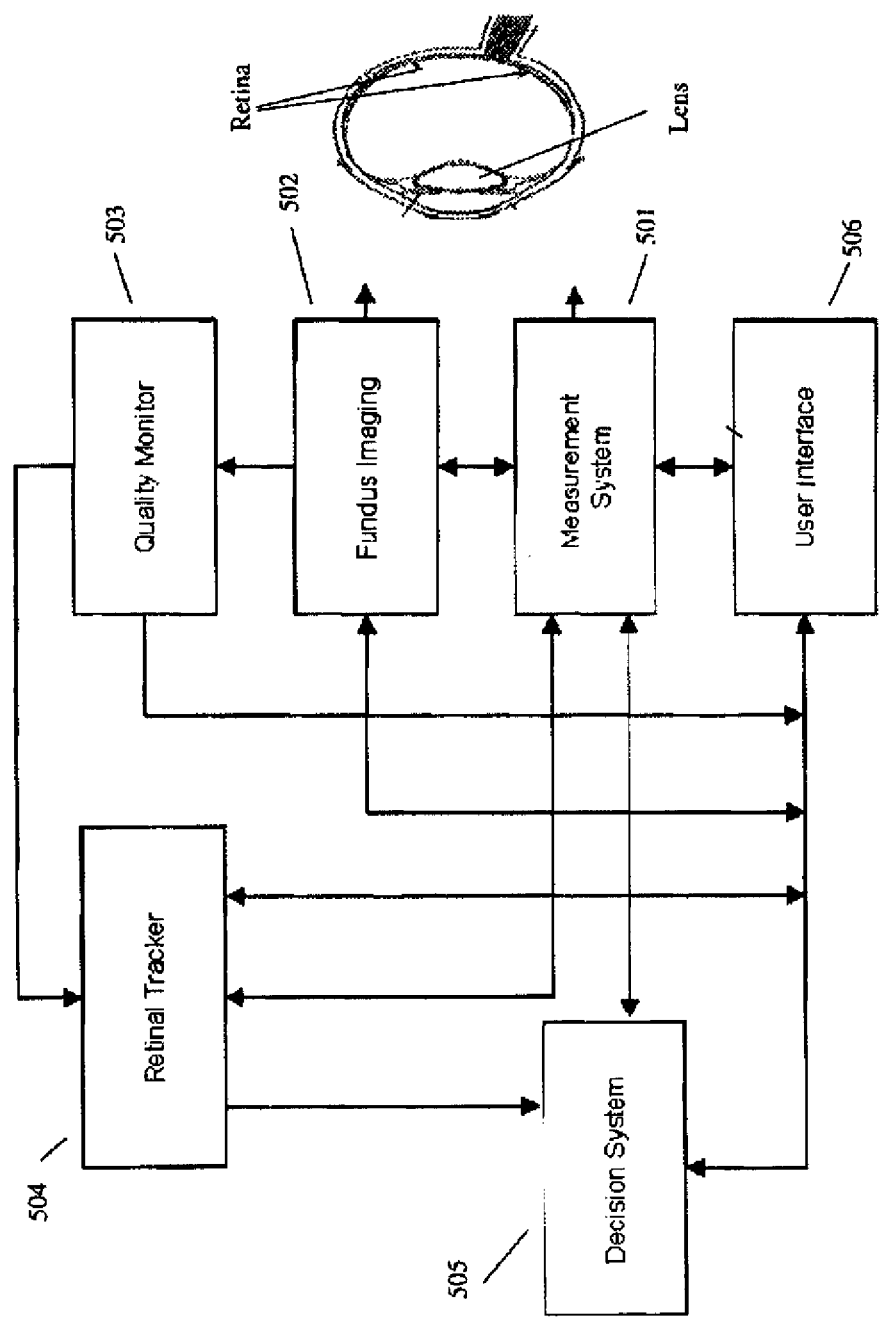

In contrast, the method described herein relies on tracking based information to decide the placement of multiple small FOV scan patterns with contiguous boundaries. Sophisticated registration or montaging algorithms are not required because the tracking information is used to dynamically correct for eye motion, tilt and angle changes during multiple scan cubes. For example, retinal tracking can enable adjustment of starting spatial coordinates with respect to the reference point on the retinal surface for a scan pattern with a given geometry. Pre-defined spatial positions can be selected as the starting point for a given scan volume with fixed dimensions such that multiple data volumes can be combined together with an adjustable level of overlap at the boundary. FIG. 4 shows the enface image obtained by a tracking enabled composite scan pattern (3×1). The enface image from each cube was montaged automatically using an autocorrelation based approach. It is clear from the montage image that retinal tracking helps and corrects for eye motion even for extended period scans. FIG. 6 shows the workflow for the acquisition of the given composite scan pattern (3×1) for collection of OCT angiography data. After an initial alignment of the patient and scan type selection, each data cube is collected and the patient is allowed to sit back from the instrument and relax between the long scans because the system is capable of recognizing where the last scan was taken and positioning the next scan accordingly. This scan acquisition and analysis pattern could be accomplished by a single "click", button press, or other type of interaction with the user interface of the device.

Retinal tracking based montaging of multiple en face images generated from multiple phase-contrast data sets has several advantages. A priori knowledge of the spatial coordinates of the en face images makes it easier to stitch multiple images. For example, the data acquisition times for an image with FOV of 3 mm×1.2 mm can be longer than that of the standard cube data sets with FOV of 6 mm×6 mm. Hence it is desirable to be able to obtain multiple OCT angiography data sets that can be automatically stitched together to provide a larger FOV image without any sophisticated post-processing.

Although various embodiments that incorporate the teachings of the present invention have been shown and described in detail herein, those skilled in the art can readily devise many other varied embodiments that still incorporate these teachings and may not require all of the above described elements to fall within the scope of the invention. While the descriptions have focused on retinal OCT angiography using an image based retinal tracking system, the basic concepts could be applied to any functional OCT imaging modality and motion tracking system.

The following references are hereby incorporated by reference:

US Patent Documents

U.S. patent application Ser. No. 13/433,127 filed Mar. 28, 2012 Iyer et al., "Systems and Methods for Efficiently Obtaining Measurements of the Human Eye using Tracking"
U.S. patent application Ser. No. 13/458,933 filed Apr. 27, 2012 Horn et al., "Ultra Wide-Field Optical Coherence Tomography"
U.S. Pat. No. 6,736,508 Xie et al., "Tracking Assisted Optical Procedure"
U.S. Pat. No. 6,726,325 Xie et al., "Tracking Assisted Optical Coherence Tomography"
U.S. Pat. No. 6,325,512 Wei et al., "Retinal Tracking Assisted Optical Coherence Tomography"
U.S. Pat. No. 7,805,009 Everett et al., "Method and Apparatus for Measuring Motion of a Subject Using a Series of Partial Images from an Imaging System"

Non-Patent Literature

T. Klein et al., "The effect of micro-saccades on the image quality of ultrawide-field multimegahertz OCT data," SPIE Photonices West 2012, Paper #8209-13 (2012)
Y. Li et al., "Automatic montage of SD-OCT data sets,", Optics Express, 19, 26239-26248 (2011)
Leitgeb et al. "Ultrahigh resolution Fourier domain optical coherence tomography," *Optics Express* 12(10):2156 (2004)

R. J. Zawadski et al. "Cellular resolution volumetric in vivo retinal imaging with adaptive optics-optical coherence tomography" Optics Express 17(5); 4084 2009.

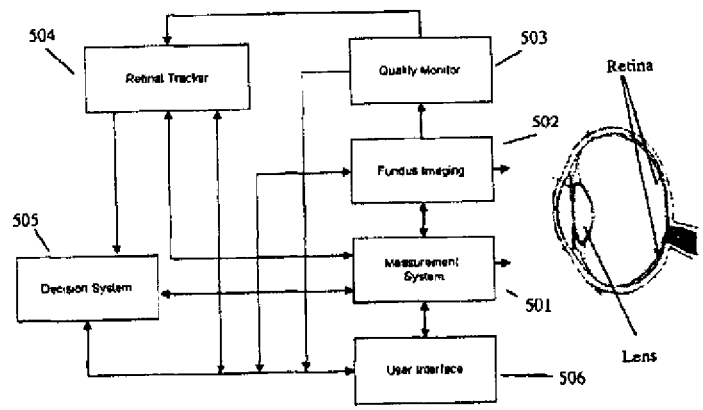

What is claimed is:

1. A method of collecting and analyzing functional OCT imaging data of an eye of a patient, said method comprising:
    acquiring a plurality of OCT measurement data from the eye of a patient, said measurements being acquired by scanning the eye with a beam of light using a scanning device;
    monitoring the eye position to detect transverse motion while acquiring the plurality of measurement data, and wherein the eye position information is used to control the direction of the scanning device to ensure that at least two OCT measurements are acquired when the scanned beam of light is at the same position on the eye even if the eye has moved between the two measurements;
    analyzing the change between the at least two OCT measurements to identify blood flow; and
    storing or displaying information related to the identified blood flow.

2. A method as recited in claim 1, wherein measurement data is rejected if eye motion has caused it to be displaced relative to another measurement.

3. A method as recited in claim 1, wherein measurement data from the same location are re-acquired if the eye position monitoring detects motion during the acquisition.

4. A method as recited in claim 1, wherein the measurement data are A-scans.

5. A method as recited in claim 1, wherein the measurement data are B-scans.

6. A method of collecting and analyzing functional OCT imaging data of the retina of the eye, said method comprising:
    acquiring a set of OCT data of the retina comprising a plurality of cluster scans, wherein each cluster scan comprises at least four B-scans covering approximately the same transverse locations on the retina;
    monitoring the eye position to detect transverse motion while acquiring each cluster scan, and wherein all the measurements associated with a particular cluster scan are rejected if eye motion has occurred during the acquisition of any individual B-scan within that particular cluster scan;
    analyzing the remaining measurement data to determine motion contrast; and
    displaying an image illustrating the motion contrast.

7. A method as recited in claim 6, wherein a cluster scan is re-acquired if the eye position monitoring detects motion during the acquisition.

8. A method as recited in claim 6, wherein the eye position monitoring is accomplished by a fundus imaging based tracking system.

9. A method as recited in claim 8, wherein the update rate of the imaging system is synchronized to the time required to acquire a single cluster scan.

10. A method of collecting and analyzing large field of view functional OCT imaging data of an eye of a patient, said method comprising:
    acquiring a large field of view data set of the eye comprising at least two smaller field of view data sets, wherein each smaller data set is centered on a different location within the eye;
    monitoring the eye position while acquiring the smaller data sets, and wherein, the location of the acquisition of each of the smaller data sets is determined based in part on the monitored eye position;
    combining the smaller field of view data sets to define the large field of view data set, the combination being based on information derived from the monitoring step;
    analyzing the combined multiple data sets to identify blood flow; and
    displaying an image based on the identified blood flow.

11. A method as recited in claim 10, wherein the eye position monitoring accounts for transverse motion during data acquisition.

12. A method as recited in claim 10, wherein the eye position monitoring accounts for tilt changes occurring during data acquisition.

13. A method as recited in claim 10, wherein the eye position monitoring accounts for angle changes during data acquisition.

14. A method as recited in claim 10, wherein the displayed image is a composite en face vasculature image.

15. A method as recited in claim 10, wherein the patient is allowed to sit back from the instrument between acquisition of the at least two data sets.

16. A method as recited in claim 10, wherein the data acquisition is initiated by a single interaction with a user interface and the system automatically acquires the multiple data sets without requiring further interaction with the user interface.

17. An OCT system for collecting and analyzing functional OCT image data, said system comprising:
    an OCT measurement system for acquiring a plurality of measurements from the eye of a patient, said measurement system including a scanner for scanning a beam of light over the eye;
    a tracking system for monitoring the location of the eye during the OCT measurement acquisition;
    a processor for analyzing the tracking information and for controlling the direction of the scanner of the measurement system to ensure that at least two OCT measurements are acquired when the scanned beam of light is at the same position on the eye even if the eye has moved between the two measurements, said processor for analyzing the change between the at least two OCT measurements to identify blood flow; and
    a display for displaying a vascular image of the eye based on the identified blood flow.

18. An OCT system as recited in claim 17, wherein the tracking system is a fundus imaging system.

19. An OCT system as recited in claim 17, wherein the processor instructs the OCT measurement system to re-acquire a measurement if motion exceeding a pre-defined threshold is determined.

* * * * *

UNITED STATES PATENT AND TRADEMARK OFFICE
CERTIFICATE OF CORRECTION

PATENT NO. : 8,857,988 B2
APPLICATION NO. : 13/542588
DATED : October 14, 2014
INVENTOR(S) : Utkarsh Sharma et al.

It is certified that error appears in the above-identified patent and that said Letters Patent is hereby corrected as shown below:

Delete title page and substitute the attached title page therefor.

On the Title Page

On page 2, in column 2, under "Other Publications", line 7, delete "Photonices" and insert -- Photonics --, therefor.

In the Drawings

Delete drawing sheet 3 of 4, and substitute the attached drawing sheet 3 of 4, therefor.

On sheet 3 of 4, in Figure 5, Reference Numeral 506, line 1, delete "nterface" and insert -- interface --, therefor.

In the Specification

In column 2, line 21, delete "Photonices" and insert -- Photonics --, therefor.

In column 6, line 44, delete "minor" and insert -- mirror --, therefor.

In column 7, line 5, delete "minor." and insert -- mirror. --, therefor.

In column 8, line 36, delete "minors" and insert -- mirrors --, therefor.

In column 10, line 62, delete "Photonices" and insert -- Photonics --, therefor.

Signed and Sealed this
Tenth Day of February, 2015

Michelle K. Lee
*Deputy Director of the United States Patent and Trademark Office*

(12) United States Patent
Sharma et al.

(10) Patent No.: US 8,857,988 B2
(45) Date of Patent: Oct. 14, 2014

(54) DATA ACQUISITION METHODS FOR REDUCED MOTION ARTIFACTS AND APPLICATIONS IN OCT ANGIOGRAPHY

(75) Inventors: Utkarsh Sharma, San Ramon, CA (US); Matthew J. Everett, Livermore, CA (US)

(73) Assignee: Carl Zeiss Meditec, Inc., Dublin, CA (US)

(*) Notice: Subject to any disclaimer, the term of this patent is extended or adjusted under 35 U.S.C. 154(b) by 6 days.

(21) Appl. No.: 13/542,588

(22) Filed: Jul. 5, 2012

(65) Prior Publication Data
US 2013/0176532 A1  Jul. 11, 2013

Related U.S. Application Data

(60) Provisional application No. 61/505,483, filed on Jul. 7, 2011, provisional application No. 61/645,464, filed on May 10, 2012.

(51) Int. Cl.
*A61B 3/10* (2006.01)
*A61B 5/00* (2006.01)

(52) U.S. Cl.
CPC .............. *A61B 3/102* (2013.01); *A61B 5/0066* (2013.01)
USPC ......................... 351/209; 351/206; 351/246

(58) Field of Classification Search
USPC ............... 351/200–246; 396/18, 51; 600/425; 382/130, 131
See application file for complete search history.

(56) References Cited

U.S. PATENT DOCUMENTS

| | | | |
|---|---|---|---|
| 4,135,791 A | 1/1979 | Govignon | |
| 4,213,678 A | 7/1980 | Pomerantzeff et al. | |
| 4,732,466 A | 3/1988 | Humphrey | |
| 4,768,873 A | 9/1988 | Webb | |
| 4,768,874 A | 9/1988 | Webb et al. | |
| 4,856,891 A | 8/1989 | Pflibsen et al. | |
| 4,937,526 A | 6/1990 | Ehman et al. | |
| 5,321,501 A | 6/1994 | Swanson et al. | |
| 5,471,303 A | 11/1995 | Ai et al. | |
| 5,575,286 A | 11/1996 | Weng et al. | |
| 5,644,642 A | 7/1997 | Kirschbaum | |

(Continued)

FOREIGN PATENT DOCUMENTS

EP  2147634 A1  1/2010
WO  03/105678 A2  12/2003

(Continued)

OTHER PUBLICATIONS

International Search Report and Written Opinion received for PCT Patent Application No. PCT/EP2012/063191, mailed on Dec. 4, 2012, 8 pages.

(Continued)

*Primary Examiner* — Darryl J Collins
*Assistant Examiner* — Gary O'Neill
(74) *Attorney, Agent, or Firm* — Morrison & Foerster LLP

(57) ABSTRACT

Systems and methods for reducing the effects of motion on functional optical coherence tomography (OCT) imaging are described. Embodiments including post-processing and motion tracking are presented. A preferred embodiment in which functional OCT data is collected and analyzed for motion as a multiple scan unit is described. An extension of the invention to the collection of large field of view or montaged functional OCT data sets is also presented.

19 Claims, 4 Drawing Sheets